United States Patent [19]

De Garie et al.

[11] Patent Number: 4,672,691
[45] Date of Patent: Jun. 16, 1987

[54] BULK VOLUME FERMENTER

[75] Inventors: Claude De Garie; Albert Cocci; Robert C. Landine, all of Fredericton, Canada

[73] Assignee: Adi Limited, New Brunswick, Canada

[21] Appl. No.: 805,801

[22] Filed: Dec. 6, 1985

[51] Int. Cl.$^4$ .............................................. E04H 3/19
[52] U.S. Cl. .......................................... 4/499; 4/501; 48/197 A; 210/218
[58] Field of Search ...................... 48/197 A; 210/218; 126/415; 4/499, 501

[56] References Cited

U.S. PATENT DOCUMENTS

3,330,118 7/1967 Biais ........................................ 4/498
3,933,628 1/1976 Varani ................................. 126/415

Primary Examiner—Carroll B. Dority, Jr.
Attorney, Agent, or Firm—Shoemaker and Mattare, Ltd.

[57] ABSTRACT

A fermentation pond has a cover and gas-collection system that includes a gas-impermeable membrane resistant to the elements and resistant to chemical deterioration by both the contents of the pond and any biogas generated by fermentation in the pond. The membrane overlies the full surface of the pond. A biogas collection conduit is positioned at the surface of the pond and under the membrane, and weights are located so as to urge the membrane downwardly along lines separated from each other so as to define between the lines a plurality of channels along which biogas can pass to the collection conduit.

16 Claims, 7 Drawing Figures

BULK VOLUME FERMENTER

FIELD OF THE INVENTION

The present invention relates to an earthen, membrane-covered, anaerobic fermentation pond, often referred to as a Bulk Volume Fermenter. Such covered ponds are specifically designed to improve fermentation and monitoring, and to recover the biogas by-product of this fermentation.

BACKGROUND OF THIS INVENTION

Anaerobic digestion has been frequently used by industries and by municipalities to treat their wastes. Generally, they consist of digesters requiring extensive controls to regulate temperature, pH, alkalinity and other parameters to maintain the efficiency of the fermentation in these expensive, high-rate digesters.

Digesters are well suited for municipal effluents or industries that can regulate the quantity and quality of waste to be treated. Most industries cannot control their waste discharge and have large variations in flow, composition and concentration. These fluctuations in waste characteristics are compounded by batch discharges of recirculation tanks, washup and accidental discharges. This is specifically where the Bulk Volume Fermenter is needed.

Earthen ponds have also been extensively used for other methods of wastewater treatment such as flow equalization, holding pond, aerated lagoon, stabilization (natural) ponds and sludge ponds.

In other areas, earthen ponds or reservoirs holding potable water have used membrane liners and covers. Liners are used to reduce water leakage into the soil, and covers are used to produce a liquid-tight seal against water contamination. Some have used the same cover membranes to cover wastewater ponds, to control the odours of effluents, manures, or natural digestion, with varying degrees of success.

SUMMARY OF THE INVENTION

The present invention provides an earthen pond with a membrane cover specifically designed to treat the wastewater by anaerobic fermentation (with biogas recovery) in lieu of a costly digester tank normally required for this process.

More particularly, this invention provides, for use with a fermentation pond, a cover and gas-collection system comprising:

a gas-impermeable membrane resistant to the elements and resistant to chemical deterioration by both the contents of the pond and any biogas generated by fermentation in the pond, the membrane overlying substantially the full surface of the pond, a biogas collection conduit positioned at the water surface of the pond and under the membrane, and weight means positioned so as to urge the membrane downwardly along a plurality of lines separated from each other so as to define between the lines a plurality of channels along which biogas can pass to the collection conduit.

GENERAL DESCRIPTION OF THE DRAWINGS

One embodiment of this invention is illustrated in the accompanying drawings, in which like numerals denote like parts throughout the several views, and in which.

DETAILED DESCRIPTION OF THE DRAWINGS

Figures 1, 2:
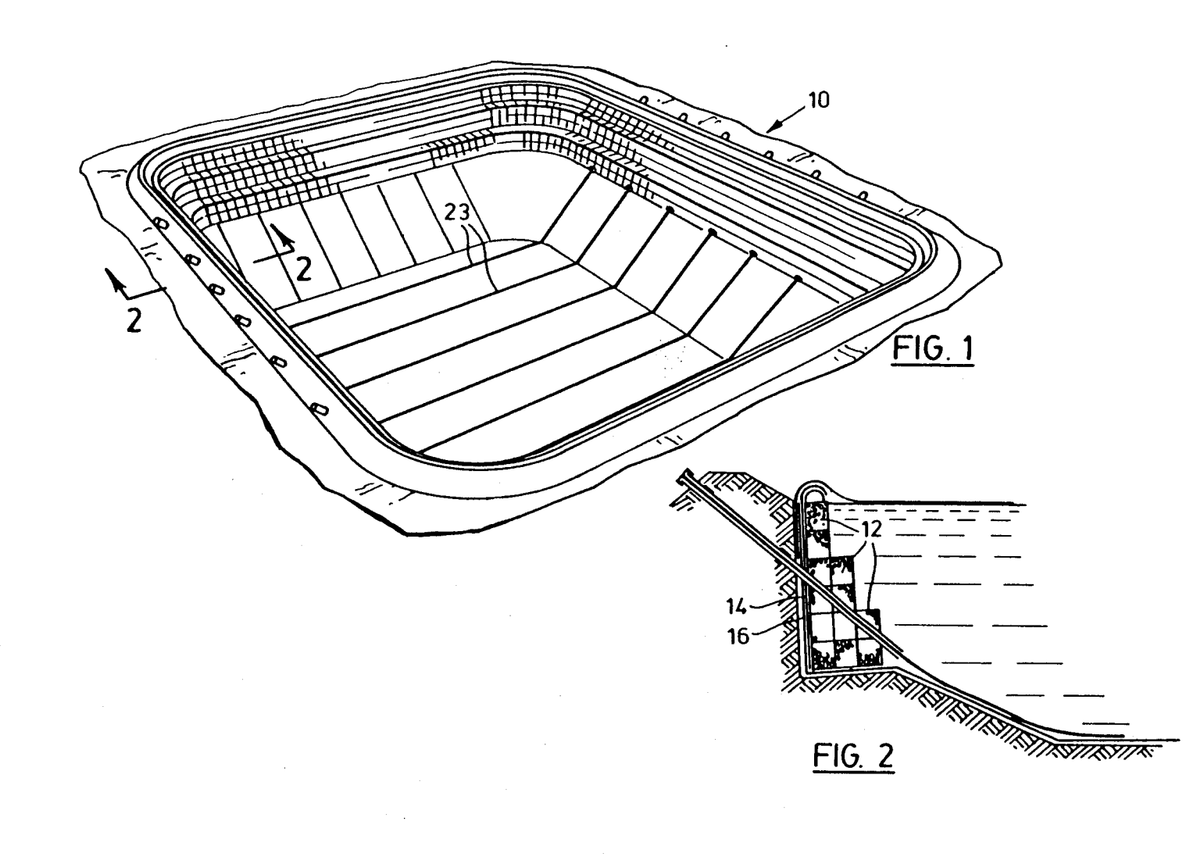
FIG. 1 is a perspective view of an excavated pond site, with which the present invention can be practised.
FIG. 2 is a sectional view taken at the line 2—2 in FIG. 1.
Figures 3, 4:
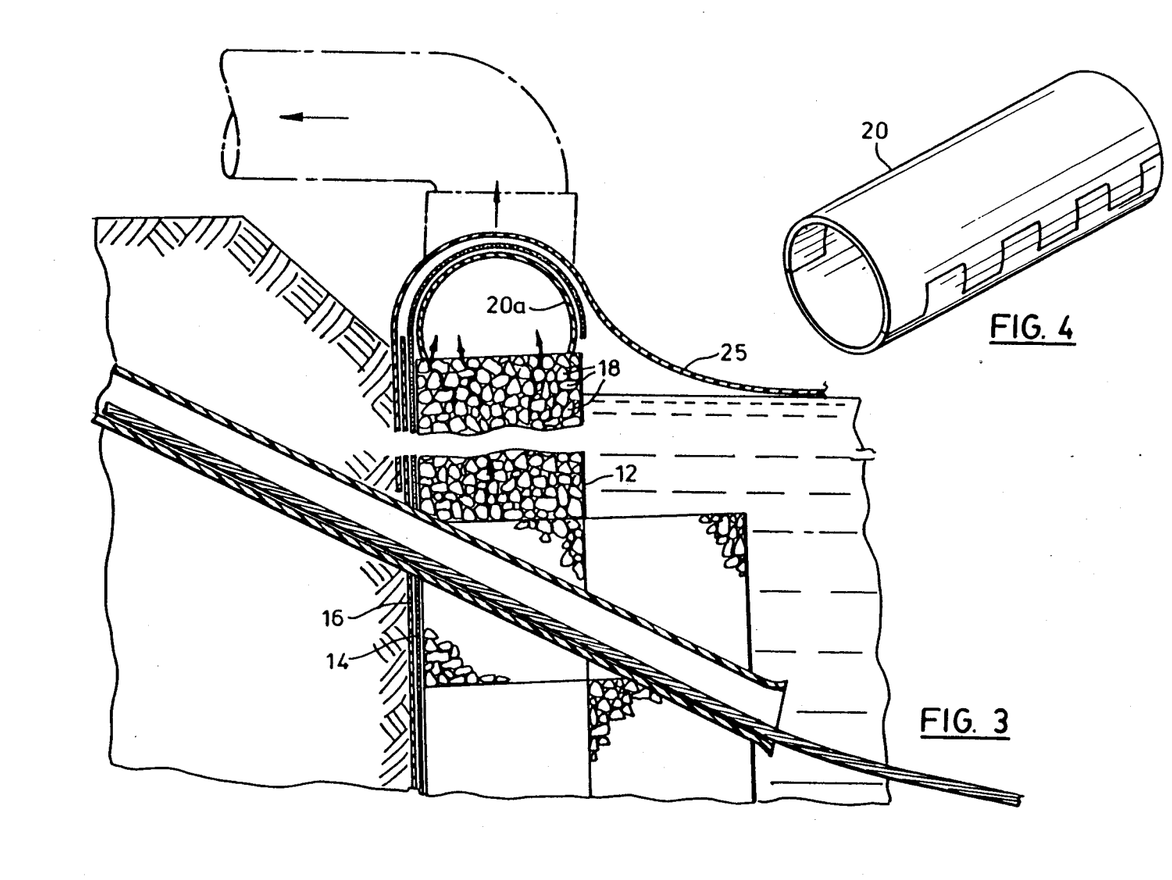
FIG. 3 is an enlarged view of a portion of the sectional view of FIG. 2.
FIG. 4 is a partial perspective view of a cylindrical member showing how it can be cut to construct the section shown in FIG. 3.

The earthen pond or Bulk Volume Fermenter (BVF) is constructed by excavating a site shown generally at 10 in FIG. 1, including backfill of on-site materials. The steepness of the internal slopes is determined by the soil conditions. The top two to six meters of the pond are constructed vertically with rock-filled baskets, as best seen in the sectional view of FIG. 2. The baskets 12 are constructed of non-corrosive, high-density polyethylene mesh. When required, a felt material 14 and an impermeable membrane 16 are placed under the rock-filled baskets and up the back side thereof, as seen in FIG. 2. The rock-filled baskets become an integral part of the fermentation process, with the rock providing a surface for the anaerobic bacteria to attach themselves, hence providing a better degree of treatment. The rock-filled baskets 12 leave sufficient voids around the rocks 18 for biogas to escape vertically along the perimeter of the pond. A pipe 20 seen in FIG. 4 is cut in saw-tooth configuration to provide two semi-cylinders with the saw-tooth configuration along the edges. One of the portions is attached to the top of the rock-filled baskets 12, as seen at 20a in FIG. 3. The pipe portion 20a collects the biogas which is generated. The biogas naturally migrates upwards in the rock voids and into the pipe. From there, it is drawn off by suction blowers (not illustrated) which may be located at points of maximum biogas production along this collector pipe. The assistance of blowers is known technology, and does not form the focus of the present invention. The blowers are there only to direct the biogas to its end use.

As seen in FIG. 1, the floor of the pond 10 may contain many pipes 23, each with a plurality of outlets in order to allow effluent to be well distributed in and out of the pond. This is known technology, and does not lie at the focus of the present invention.

The pond may also be provided with slow-speed mixers in the form of large-diameter propellers, lowered into the pond on guide rails. These have not been illustrated, as they are known technology.

Figure 5:
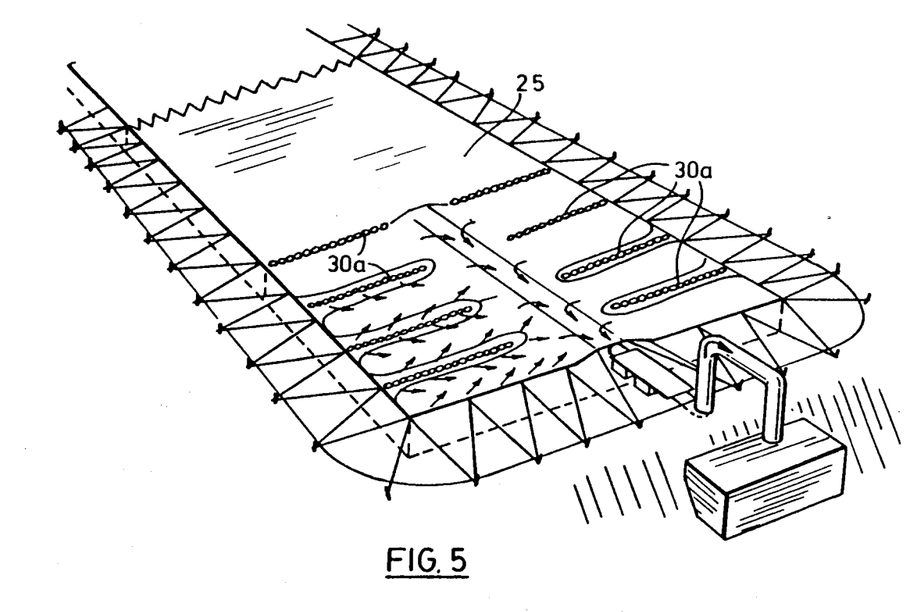
FIG. 5 is a perspective view of a pond, showing the cover and gas-collection system provided in this invention.
Figure 6:
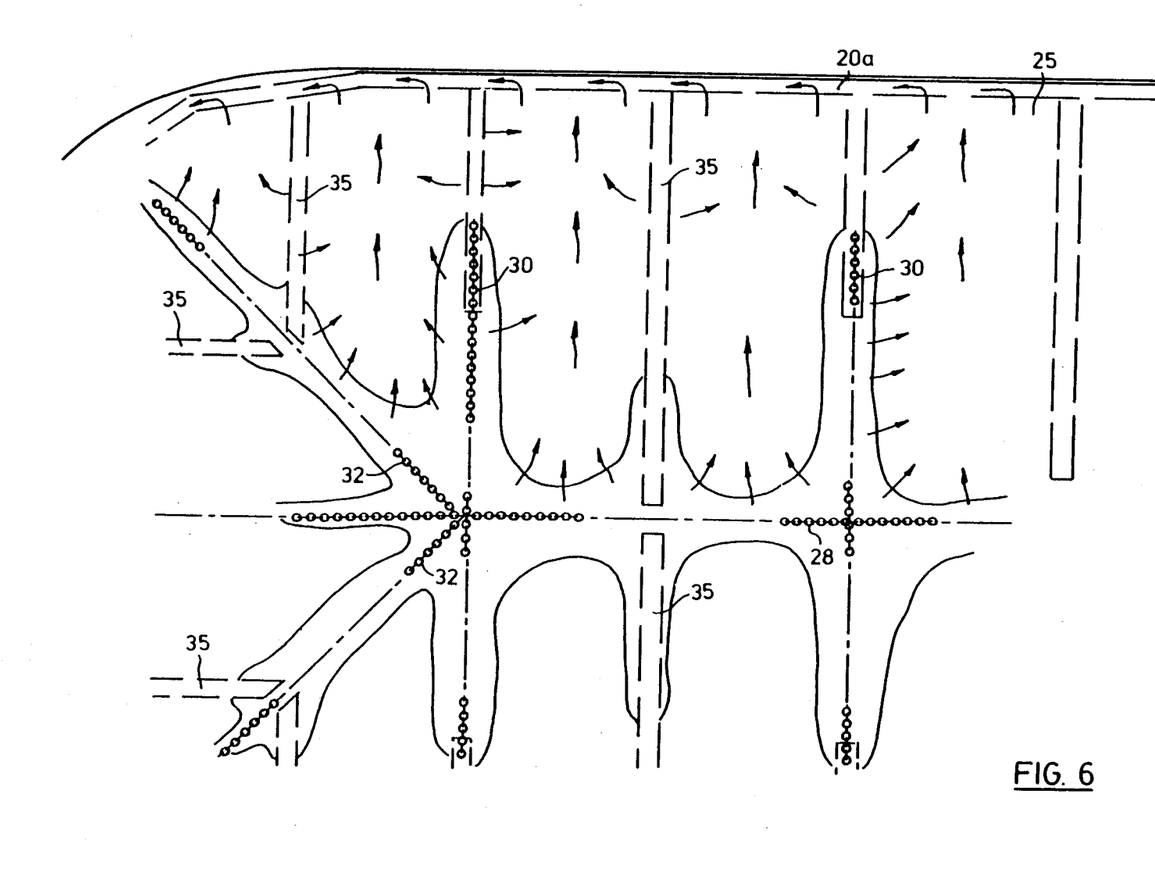
FIG. 6 is a partial plan view of one form of the cover and gas-collection system.

The pond cover, illustrated in FIGS. 3, 5 and 6 consists of a membrane 25 specifically designed to operate as an integral part of the anaerobic fermenter. The composition of the membrane is chosen to resist attack by the weather and the waste being treated, as well as by the biogas generated. Essentially, the cover provides a means of collecting the biogas rising to the water surface. It is not intended to be a liquid-tight cover membrane. Biogas collection is accomplished by providing a series of weights, which in the illustrated embodiment consist of a plurality of weight lines, such as chains, arranged substantially perpendicularly to the biogas collection conduits constituted by the pipe portions 20a. The weight lines force the biogas to the collection conduit.

Two different variants of weight arrangement are shown in the drawings. In FIG. 6, the collection conduit constituted by the pipe portions 20a runs around the periphery of the pond, and the weight lines include a longitudinal central reach 28, and a plurality of lateral reaches 30 extending perpendicularly to either side of the reach 28, together with diagonal reaches 32 at the corners for rainwater collection.

Interspersed with the various reaches of weight lines in FIG. 6 are flotation devices, the flotation devices being arranged parallel to the weight lines so as not to block the biogas migration to the collection pipes. The flotation devices ensure that the membrane, if ruptured, will not sink.

Specifically, in FIG. 6 can be seen a plurality of lines 35 of float devices which may be in the form of rigid closed-cell plastic foam, such as ETHAFOAM (Trade Mark).

It will be understood that the chains illustrated in FIG. 6 are merely illustrative of a suitable weight material. Naturally, cables, jacketed materials and other heavy substances could also be utilized to provide the weight.

It has been stated that the floats function primarily to prevent sinking of the membrane. When the membrane is torn, and with the total cover system remaining buoyant due to the float devices, it is possible to lift the tear above the water surface, pump the accumulated water from the surface, and complete the cover repair by patching.

As can be seen in FIG. 3, the perimeter of the membrane 25 can be draped over the collector conduit pipe 20a and lowered behind the rock-filled basket 12 to a location below the low water level of the pond. This provides a water break or a sure seal against biogas escaping to the atmosphere. The cover edge is then held in place by earth backfill. In areas where rodents are a problem, a deflector plate (not illustrated) may also be added to prevent access of rodents to the membrane material.

In FIG. 5, an arrangement is shown in which the collection of biogas takes place longitudinally and centrally of the elongated cover. The biogas-collection conduit in this case is defined not by a specific section of pipe, but rather by gaps left between adjacent but separated flotation blocks, such as those shown at 37 in FIG. 7. The floats 37 are separated both longitudinally and laterally, so that biogas can enter the central longitudinal conduit under the cover 25 through the longitudinal gaps, from the side collection pockets defined between the weight lines 30a seen in FIG. 5 In the FIG. 5 embodiment, no collection takes place along the perimeter of the pond.

Figure 7:
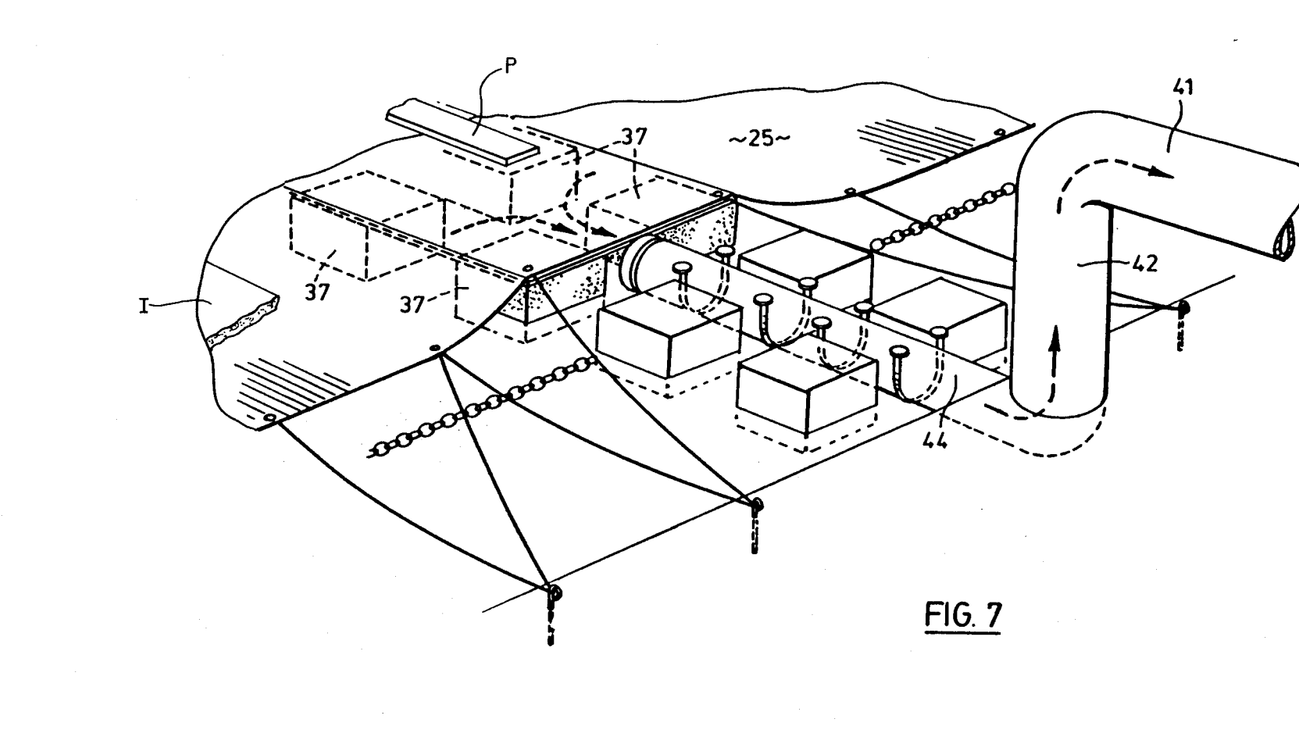
FIG. 7 is a perspective view of a portion of the gas-collection system.

If desired, planks may be placed over the floats 37 in order to provide a walkway down the centre of the cover 25.

Also, it may be desirable to provide the cover with a layer of insulation I as shown in FIG. 7, to keep the contents warm and prevent excessive heat loss in cold weather.

FIG. 7 shows portions of an aspirating means for exhausting the gaseous contents of the central collection conduit defined between and by the floats 37. A pipe portion 41 is sloped leftwardly to allow the return of condensation to the bulk volume fermenter, and is connected at the downstream end to an upstanding pipe 42, in turn connected to a horizontal pipe 44 which communicates with the space between the adjacent float blocks 37 under the cover 25. Planke P as shown in FIG. 7 are provided over the float blocks 37 to provide a walkway. The cover is arranged to ensure that the biogas under it enters the pipe 44 without any escape, and is thus sealed around the pipe 44. In regard to the insulation mentioned previously, a flexible foam insulation may be utilized, varying from 10 mm to 50 mm in thickness. This may be placed almost continuously under or over the cover 25.

The insulation material may be tied and glued in place.

When rocks of the kind shown in FIGS. 2 and 3 are not available at or close to the site of the pond, they may be replaced with an earthen or concrete wall, or steel piles. An earthen wall may be steepened using soil stabilizers, grout finish or reinforced-earth techniques. When these methods are not possible or there is insufficient land, a partial vertical wall may be constructed.

An enhanced surface area for bacteria to adhere to may be provided by sheets of fabric suspended in the body of the liquid. This technique is not shown, as it is known in the art. The fabric may be composed of polyesters, particular woven polyester with edge reinforcement of sufficient tensile strength to allow it to hang under the cover with a minimum of framing. The woven polyester may be coated with 3 mm of felt on each side, which is bonded to the weave by needle punching it from both sides. The felt is added to allow the anaerobic bacteria to attach to it and provide better treatment. The sheets are ideally placed vertically in drapes to allow the treated effluent to reach the discharge header and at the same time allow the biogas to migrate to the top. Such sheets would allow three simultaneous flow directions, similar to the rock media, without affecting the performance of the fermenter.

For some industrial effluents, it may be necessary to fill most of the pond volume with drapes of fabric sheets. In this case, a sludge rake may be required to physically scrape the sludge accumulating on the floor of the pond.

Where the perimeter of a cover membrane ends 2 to 5 meters short of reaching the water's edge, the perimeter may be provided with a fabric skirt to trap the biogas, with a skirt weight ensuring that the skirt will terminate below the water level.

While one embodiment of this invention has been illustrated in the accompanying drawings, and described hereinabove, it will be evident to those skilled in the art that changes and modifications may be made therein without departing from the essence of this invention, as set forth in the appended claims.

What is claimed is:

1. For use with a fermentation pond, a cover and gas-collection system comprising:
    a gas-impermeable membrane resistant to the elements and resistant to chemical deterioration by both the contents of the pond and any biogas generated by fermentation in the pond, the membrane overlying substantially the full surface of the pond,
    a biogas collection conduit positioned at the surface of the pond and under the membrane,
    weight means positioned so as to urge the membrane downwardly along a plurality of lines separated from each other and a plurality of rows of floats positioned between adjacent lines of weight means so as to define between the lines a plurality of channels along which biogas can pass to the collection conduit, the floats supporting off the surface of the pond the portions of the membrane adjacent the floats, to ensure that the membrane if ruptured will not sink, and aspirating means for exhausting the gaseous contents of the collection conduit.

2. The system claimed in claim 1, in which the cover membrane has affixed thereto a layer of insulation.

3. The system claimed in claim 1, in which the collection conduit is positioned centrally of the pond, with the lines of weight means extending substantially perpendicularly away from it on both sides, the membrane having a weighted peripheral skirt to restrain the escape of biogas.

4. The system claimed in claim 1, in which the collection conduit is positioned adjacent one edge of the pond, with the lines of weight means extending substantially perpendicularly away from it on one side.

5. The system claimed in claim 1, in which the weight means consists of lengths of chain.

6. The system claimed in claim 1, in which the collection conduit is defined between two adjacent but spaced apart rows of floats with planks over the floats to provide a walkway.

7. A fermentation pond having a cover and gas-collection system which comprises:
- a gas-impermeable membrane resistant to the elements and resistant to chemical deterioration by both the contents of the pond and any biogas generated by fermentation in the pond, the membrane overlying substantially the full surface of the pond,
- a biogas collection conduit positioned at the surface of the pond and under the membrane,
- weight means positioned so as to urge the membrane downwardly along a plurality of lines separated from each other so as to define between the lines a plurality of channels along which biogas can pass to the collection conduit,
- a plurality of rows of floats positioned between adjacent lines of weight means, the floats supporting off the surface of the pond the portions of the membrane adjacent the floats, and to ensure that the membrane if ruptured will not sink, and
- aspirating means for exhausting the gaseous contents of the collection conduit.

8. The invention claimed in claim 7, in which the cover membrane has affixed thereto a layer of insulation.

9. The invention claimed in claim 7, in which the collection conduit is positioned centrally of the pond, with the lines of weight means extending substantially perpendicularly away from it on both sides, the membrane having a weighted peripheral skirt to restrain the escape of biogas.

10. The invention claimed in claim 7, in which the collection conduit is positioned adjacent one edge of the pond, with the lines of weight means extending substantially perpendicularly away from it on one side.

11. The invention claimed in claim 7, in which the weight means consists of lengths of chain.

12. The invention claimed in claim 7, in which the collection conduit is defined between two adjacent but spaced apart rows of floats with planks over the floats to provide a walkway.

13. The system claimed in claim 1, wherein said aspirating means includes a pipe portion sloped to allow return of condensation to the fermentation pond.

14. The system claimed in claim 13, wherein said aspirating means further includes an upstanding pipe connected to one end of said pipe portion which is in turn connected to a horizontal pipe which communicates with the collection conduit.

15. The invention claimed in claim 7, wherein said aspirating means includes a pipe portion sloped to allow return of condensation to the fermentation pond.

16. The invention claimed in claim 15, wherein said aspirating means further includes an upstanding pipe connected to one end of said pipe portion which is in turn connected to a horizontal pipe which communicates with the collection conduit.

* * * * *

REEXAMINATION CERTIFICATE (4151st)

United States Patent [19]
De Garie et al.

[11] B1 4,672,691
[45] Certificate Issued Sep. 12, 2000

[54] BULK VOLUME FERMENTER

[75] Inventors: Claude De Garie; Albert Cocci; Robert C. Landine, all of Fredericton, Canada

[73] Assignee: ADI Group Inc., Fredericton, Canada

Reexamination Request:
No. 90/005,369, May 24, 1999

Reexamination Certificate for:
Patent No.: 4,672,691
Issued: Jun. 16, 1987
Appl. No.: 06/805,801
Filed: Dec. 6, 1985

[51] Int. Cl.[7] ..................................................... E04H 7/02
[52] U.S. Cl. ............................... 4/499; 4/501; 48/197 A; 210/218
[58] Field of Search ............................... 210/218; 4/499, 4/501; 48/197 A

[56] References Cited

U.S. PATENT DOCUMENTS

| | | | |
|---|---|---|---|
| 3,313,443 | 4/1967 | Dial et al. ................................. | 220/26 |
| 3,980,199 | 9/1976 | Kays ....................................... | 220/227 |
| 4,139,117 | 2/1979 | Dial . | |
| 4,438,863 | 3/1984 | Wilson et al. ........................... | 220/227 |
| 4,503,988 | 3/1985 | Gerber .................................... | 220/219 |
| 4,603,790 | 8/1986 | Gerber .................................... | 220/219 |

OTHER PUBLICATIONS

Letter from Schlegel Lining Technology, Inc. to FDL Foods, Inc., dated Sep. 11, 1984, consisting of a proposal for the construction of a floating cover for an anaerobic basin lagoon (8 pages), a warranty relating to the proposed project (4 pages), and two technical drawings of the proposed anaerobic cover system.

Proposal for construction of an anaerobic pond system by CH2M Hill for the J.R. Simplot Company, generally dated Jun. 1983 and consisting of "Contract Documents For Construction of the Miscellaneous Anaerobic Basin Work" (Litigation Production Nos. S0003–S00182) and ten technical drawings (Litigation Production Nos. S00183–S00192).

Schlegel Lining Technology, Inc. technical drawings entitled "Miscellaneous Details," Nov. 28, 1984.

"Project Definition Report for A.E. Staley Manufacturing Company, Sagamore Operation, 1985 Anaerobic Waste Treatment Project," Jan. 21, 1985.

"Anaerobic Treatability Study, A.E. Staley, Sagamore Operation," Mar. 1984.

Photographs of J.R. Simplot Facility in Burley, Idaho, Bates Nos. F 01388–01389 ("Early 1985," unconfirmed).

Photograph of FDL Food Inc. Facility in Dubuque, Iowa, Bates No. S 00194 (Dec. 4, 1984, unconfirmed).

"Potato Waste Biogas Helps Energy Needs," *World Wastes*, 1 page (Nov. 1984), Bates No. ADI00000172.

Preliminary Investigation into the Feasibility of Using Three Smaller BVFs vs One Larger BVF for E.A. Staley, Sagamore Operation, 54 pages (Aug. 1984), Bates Nos. ADI00003692–3717; ADI00003486–3488; ADI00004038–4061; and ADI00006023–6024.

Proposal entitled "Anaerobic Pretreatment for Niagara of Wisconsin Paper Corp.," 37 pages (Apr. 9, 1984), Bates Nos. ADI00006470–6506.

(List continued on next page.)

*Primary Examiner*—Christopher Upton
*Attorney, Agent, or Firm*—Shoemaker and Mattare, Ltd.

[57] ABSTRACT

A fermentation pond has a cover and gas-collection system that includes a gas-impermeable membrane resistant to the elements and resistant to chemical deterioration by both the contents of the pond and any biogas generated by fermentation in the pond. The membrane overlies the full surface of the pond. A biogas collection conduit is positioned at the surface of the pond and under the membrane, and weights are located so as to urge the membrane downwardly along lines separated from each other so as to define between the lines a plurality of channels along which biogas can pass to the collection conduit.

OTHER PUBLICATIONS

Robert C. Landine et al., "Anaerobic Pretreatment Facility Also Provides Sludge Disposal Capability and Source of Renewal Energy for Food Processor," Proceedings, 6*th* Symposium on Wastewater Treatment, pp. 805–815 (Nov. 1983), Bates Nos. ADI00000091–102.

Schlegel Lining Technology, Inc., Technical Drawing No. 1314–C entitled "J.R. Simplot Company Food Division, Burley, Idaho, Anaerobic Basin Floating Cover Liner Layout Sections of Basin" (Jul. 11, 1983).

Communication to Mr. R.D. Popma, Ph.D., P.E. re: ADI Anaerobic Pretreatment—Sagamore Plant, with attachments, 13 pages (Mar. 8, 1983), Bates Nos. ADI00003275–3287.

Dennis H. Gerber et al., "Floating Covers for Potable Water Reservoirs—State of the Art," *Colloque Etancheite Superficielle*, pp. 109–111 (1983).

Communication to Mr. Don Bixby re: ADI Proposal for Anaerobic Treatment of Process Plant Effluent with Appendices A–C, 11 pages (Dec. 28, 1982), Bates Nos. ADI00003288–3298.

Communication to Lexcan Industrial Supply Ltd. re: Floating Cover and Gas Collection for Harnes, France with attachments, 9 pages (Mar. 20, 1981), Bates Nos. ADI00015948–15949; ADI00015956–15957; ADI00015960; ADI00015971–15972; and ADI00021627.

Drawing, Bates No. ADI00002545 (Undated).

Exhibit A of Amendment Under 37 C.F.R. §1.53(d), filed herewith, Declaration of Claude DeGarie (4 pages), with attached letter dated Nov. 8, 1994, to Schlegel Lining Technology Inc. and enclosure to said letter (26 pages), Bates Nos. ADI00004024–4025; and ADI00004038–4061.

"Preliminary Investigation Into the Feasibility of Using Three Smaller BVFs vs. One Larger BVF" For A.E. Staley, Sagamore Operation (Aug. 1984), (Bates Nos. ADI00003685–3717) and drawings (Bates Nos. ADI00003718–3720).

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2 and 8 are cancelled.

Claims 1 and 7 are determined to be patentable as amended.

Claims 3–6 and 9–16, dependent on an amended claim, are determined to be patentable.

New claim 17 is added and determined to be patentable.

1. For use with a fermentation pond, a cover and gas-collection system comprising:
    a gas-impermeable membrane resistant to the elements and resistant to chemical deterioration by both the contents of the pond and any biogas generated by fermentation in the pond, the membrane overlying substantially the full surface of the pond, *the membrane having a layer of insulation affixed thereto,*
    a biogas collection conduit positioned at the surface of the pond and under the membrane,
    weight means positioned so as to urge the membrane downwardly along a plurality of lines separated from each other *and a plurality of rows of floats positioned between adjacent lines of weight means* so as to define between the lines a plurality of channels along which biogas can pass to the collection conduit,
    *the* floats supporting off the surface of the pond the portions of the membrane adjacent the floats, to ensure that the membrane if ruptured will not sink, and
    aspirating means for exhausting the gaseous contents of the collection conduit.

7. A fermentation pond having a cover and gas-collection system which comprises:
    a gas-impermeable membrane resistant to the elements and resistant to chemical deterioration by both the contents of the pond and any biogas generated by fermentation in the pond, the membrane overlying substantially the full surface of the pond, *the membrane having an insulation layer affixed thereto,*
    a biogas collection conduit positioned at the surface of the pond and under the membrane,
    weight means positioned so as to urge the membrane downwardly along a plurality of lines separated from each other so as to define between the lines a plurality of channels along which biogas can pass to the collection conduit,
    a plurality of rows of floats positioned between adjacent lines of weight means, the floats supporting off the surface of the pond the portions of the membrane adjacent the floats, and to ensure that the membrane if ruptured will not sink, and
    aspirating means for exhausting the gaseous contents of the collection conduit.

*17. For use with a fermentation pond, a cover and gas-collection system comprising:*
    *a gas-impermeable membrane resistant to the elements and resistant to chemical deterioration by both the contents of the pond and any biogas generated by fermentation in the pond, the membrane overlying substantially the full surface of the pond, the membrane having a layer of insulation affixed thereto,*
    *a biogas collection conduit positioned at the surface of the pond and under the membrane,*
    *weight means positioned so as to urge the membrane downwardly along a plurality of lines separated from each other and a plurality of rows of floats, the weight means positioned between adjacent rows of floats so as to define channels between the lines and floats such that a major portion of biogas passes through a central region of the channels to the collection conduit,*
    *the floats supporting off the surface of the pond the portions of the membrane adjacent the floats, to ensure that the membrane if ruptured will not sink, and*
    *aspirating means for exhausting the gaseous contents of the collection conduit.*

* * * * *